(12) United States Patent
Tamura (10) Patent No.: US 7,998,063 B2
(45) Date of Patent: Aug. 16, 2011

(54) INTRO-SUBJECT INTRODUCTION APPARATUS, EXTRACORPOREAL RECEIVING APPARATUS, AND INTRA-SUBJECT INFORMATION GATHERING SYSTEM

(75) Inventor: Kazuaki Tamura, Hachioji (JP)

(73) Assignee: Olympus Corporation, Tokyo (JP)

( * ) Notice: Subject to any disclaimer, the term of this patent is extended or adjusted under 35 U.S.C. 154(b) by 1049 days.

(21) Appl. No.: 11/888,514

(22) Filed: Aug. 1, 2007

(65) Prior Publication Data

US 2008/0033242 A1 Feb. 7, 2008

(30) Foreign Application Priority Data

Aug. 2, 2006 (JP) ................... 2006-211253

(51) Int. Cl.
*A61B 1/06* (2006.01)
(52) U.S. Cl. ........................................ 600/118
(58) Field of Classification Search .............. 600/101, 600/109, 117, 118, 160, 373, 374, 377
See application file for complete search history.

(56) References Cited

U.S. PATENT DOCUMENTS

| | | | | |
|---|---|---|---|---|
| 4,834,103 | A * | 5/1989 | Heath | 600/372 |
| 6,019,757 | A * | 2/2000 | Scheldrup | 606/49 |
| 6,115,636 | A * | 9/2000 | Ryan | 607/60 |
| 7,558,620 | B2 * | 7/2009 | Ishibashi | 600/476 |
| 2004/0138652 | A1 * | 7/2004 | Berube | 606/33 |
| 2005/0256402 | A1 * | 11/2005 | Kawashima et al. | 600/437 |
| 2006/0173265 | A1 * | 8/2006 | Kim et al. | 600/407 |
| 2006/0243288 | A1 * | 11/2006 | Kim et al. | 128/899 |
| 2007/0078324 | A1 * | 4/2007 | Wijisiriwardana | 600/386 |

FOREIGN PATENT DOCUMENTS

| | | |
|---|---|---|
| EP | 1 159 917 A1 | 12/2001 |
| JP | 2005-192821 | 7/2005 |
| JP | 2005-288184 | 10/2005 |
| JP | 2005-342083 | 12/2005 |
| JP | 2006-75269 | 3/2006 |
| JP | 2006-296971 | 11/2006 |
| WO | WO 2004/066833 | 8/2004 |
| WO | WO 2004/068748 A1 | 8/2004 |
| WO | WO 2004/088448 | 10/2004 |
| WO | WO 2005/044094 | 5/2005 |
| WO | WO 2006/038524 | 4/2006 |

OTHER PUBLICATIONS

Extended Supplementary European Search Report dated Feb. 4, 2010.

* cited by examiner

*Primary Examiner* — Philip Smith
(74) *Attorney, Agent, or Firm* — Scully, Scott, Murphy & Presser, P.C.

(57) ABSTRACT

An intro-subject introduction apparatus which is introduced into the inside of a subject and is movable inside the subject includes an information acquisition section for acquiring intra-subject information. A wireless transmission section transmits a transmission signal including the acquired intra-subject information to an extracorporeal receiving apparatus provided outside the subject. A reflected signal deriving section derives a reflected signal generated between the wireless transmission section and the inside of the subject. A transmission signal control section controls the wireless transmission section on the basis of the derived reflected signal.

9 Claims, 5 Drawing Sheets

INTRO-SUBJECT INTRODUCTION APPARATUS, EXTRACORPOREAL RECEIVING APPARATUS, AND INTRA-SUBJECT INFORMATION GATHERING SYSTEM

CROSS-REFERENCE TO RELATED APPLICATIONS

This application is based upon and claims the benefit of priority from prior Japanese Patent Application No. 2006-211253, filed Aug. 2, 2006, the entire contents of which are incorporated herein by reference.

BACKGROUND OF THE INVENTION

1. Field of the Invention

The present invention relates to an intro-subject introduction apparatus which is introduced into the inside of a subject, moves within the inside of the subject, and acquires intra-subject information, an extracorporeal receiving apparatus which is arranged outside the subject and acquires intra-subject information acquired by the intro-subject introduction apparatus, and an intra-subject information gathering system including these apparatuses.

2. Description of the Related Art

At present, a deglutition type endoscope, i.e., a so-called capsule type endoscope (intro-subject introduction apparatus) is put to practical use in the field of endoscopy. Such a capsule type endoscope is provided with an imaging function and a wireless communication function. Further, the capsule type endoscope, after it is swallowed from a mouth of a subject for the purpose of observation (examination) until it is naturally excreted from the body of the subject, moves through the inside of a body cavity, i.e., through the inside of internal organs such as a stomach and small intestine in accordance with the peristaltic movement and performs imaging.

Image data items imaged by the capsule type endoscope in the body of the subject while the endoscope moves through the body cavity are transmitted in sequence to the extracorporeal receiving apparatus provided outside the subject by wireless communication, and stored in a memory provided externally via the extracorporeal receiving apparatus. By carrying such an extracorporeal receiving apparatus having a wireless communication function and memory function with the subject, the subject can freely move after the subject swallows the capsule type endoscope until the capsule is excreted from the body of the subject.

As one of wireless communication systems in the capsule type endoscope, a human body communication system is proposed in which a subject is utilized as a signal transmission medium so as to transmit image data to the outside of the subject. For example, in a human body communication system proposed in International Publication No. 2004/068748, two electrodes for signal transmission are provided on an outer surface of a capsule type endoscope. A potential difference corresponding to image data is generated between signal transmitting electrodes, thereby causing an electric current to flow from the inside of a subject to the outside of the subject. Further, the current is detected by receiving electrodes of an extracorporeal receiving apparatus arranged outside the subject. As a result, it becomes possible to transmit image data by utilizing a human body as a signal transmission medium.

Here, a conventional intra-subject information gathering system utilizing a human body communication system has a problem of a lack of stability in communication. The conventional intra-subject information gathering system utilizing a human body communication system has a configuration in which transmitting electrodes are arranged on the outer surface of the capsule type endoscope. Since the capsule type endoscope having such a configuration moves through the inside of the subject, there is therefore a possibility that the condition of contact between the transmitting electrodes and the inside of the subject changes. If the condition of contact between the transmitting electrodes of the capsule type endoscope and the inside of the subject changes, the output impedance viewed from the transmitting electrodes also changes. As a result, a mismatch is caused between the transmitting electrodes and the subject with respect to the impedance variation amount. Further, there is a possibility of a phenomenon in which loss of transmission signal power of the capsule type endoscope is caused being brought about.

In the conventional capsule type endoscope, a control method for the output impedance variation amount resulting from the contact condition of the transmitting electrodes is not taken into consideration. Accordingly, it is conceivable that the loss of the transmission signal power brings about lowering of the received signal level and liability to an influence of noise, and therefore that the intra-subject information gathering system cannot deal with maintenance of communication stability.

BRIEF SUMMARY OF THE INVENTION

An object of the present invention is to provide an intro-subject introduction apparatus, an extracorporeal receiving apparatus, and an intra-subject information gathering system capable of performing stable communication by reducing a power loss amount with respect to varying output impedance of transmitting electrodes.

According to a first aspect of the present invention, there is provided an intro-subject introduction apparatus which is introduced into the inside of a subject and is movable inside the subject, comprising: an information acquisition which acquires intra-subject information; a wireless transmission section which transmits a transmission signal including the acquired intra-subject information to an extracorporeal receiving apparatus provided outside the subject; a reflected signal deriving section which derives a reflected signal generated between the wireless transmission section and the inside of the subject; and a transmission signal control section which controls the wireless transmission section on the basis of the derived reflected signal.

According to a second aspect of the present invention, there is provided an extracorporeal receiving apparatus arranged outside a subject, comprising: a wireless receiving section which receives a transmission signal including intra-subject information from an intro-subject introduction apparatus which is introduced into the inside of a subject and is movable inside the subject; a matching signal generating section which generates a matching signal for a match between the wireless receiving section and the subject; a reflected signal deriving section which derives a reflected signal of a matching signal generated between the wireless receiving section and the subject; and a received signal control section which controls the wireless receiving section on the basis of the derived reflected signal.

According to a third aspect of the present invention, there is provided an intra-subject information gathering system comprising: an intro-subject introduction apparatus which is introduced into the inside of a subject and is movable inside the subject, including: (a) an information acquisition section which acquires intra-subject information; (b) a wireless transmission section which transmits a transmission signal including the intra-subject information acquired by the information acquisition section; (c) a transmitting side reflected signal deriving section which derives a reflected signal generated between the wireless transmission section and the inside of the subject; and (d) a transmission signal control section which controls the wireless transmission section on the basis of the reflected signal derived by the transmitting side reflected signal deriving section; and an extracorporeal receiving apparatus arranged outside the subject, including: (a) a wireless receiving section which receives the transmission signal from the intro-subject introduction apparatus; (b) a matching signal generating section which generates a matching signal for a match between the wireless receiving section and the subject; (c) a receiving side reflected signal deriving section which derives a reflected signal of a matching signal generated between the wireless receiving section and the subject; and (d) a received signal control section which controls the wireless receiving section on the basis of the reflected signal derived by the receiving side reflected signal deriving section.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will be described below with reference to the accompanying drawings.

Figure 1:
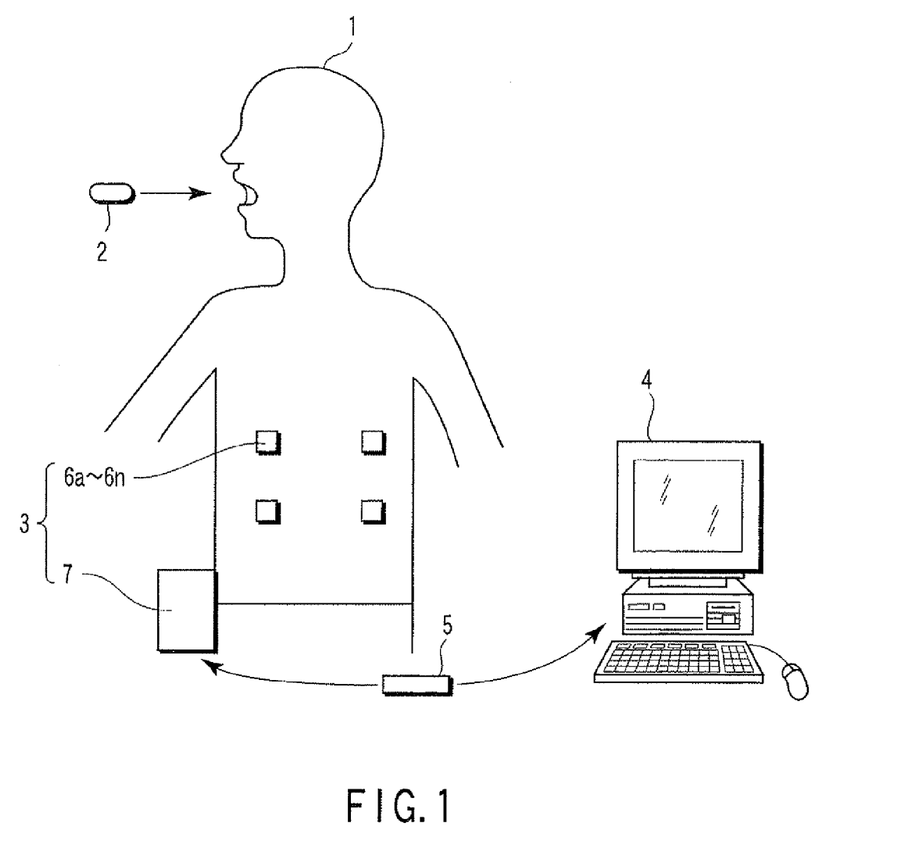
FIG. 1 is an overall configuration view of an intra-subject information gathering system according to an embodiment of the present invention.

FIG. 1 is an overall configuration view of an intra-subject information gathering system according to the embodiment of the present invention. As shown in FIG. 1, the intra-subject information gathering system comprises a capsule type endoscope 2, an extracorporeal receiving apparatus 3, a display device 4, and a portable type recording medium 5.

The capsule type endoscope 2 which functions as an example of an intro-subject introduction apparatus is introduced into the inside of a subject 1, repeatedly performs imaging while moving through the inside of the subject 1, thereby acquiring intra-subject information, and transmits a transmission signal of a predetermined frequency including the acquired intra-subject information to the extracorporeal receiving apparatus 3. The intra-subject information is, for example, an image of the inside of the subject 1.

The extracorporeal receiving apparatus 3 receives the transmission signal from the capsule type endoscope 2, and derives an image from the received signal. As shown in FIG. 1, the extracorporeal receiving apparatus 3 is provided with receiving electrodes 6a to 6n, and a processor 7. The receiving electrodes 6a to 6n are electrodes which are arranged on the outer surface of the subject 1, and used to receive a transmission signal from the capsule type endoscope 2. The processor 7 derives an image of the inside of the subject 1 from the signal received at the receiving electrodes 6a to 6n.

The display device 4 displays an image or the like of the inside of the subject 1 obtained by the capsule type endoscope 2. The display device 4 is configured as a workstation or the like for displaying an image on the basis of data obtained by the portable type recording medium 5. More specifically, the display device 4 has a function of reproducing an image signal from data recorded on the portable type recording medium 5 and displaying the reproduced image signal on a CRT display, liquid crystal display, and the like. Further, a printer or the like may be provided in place of the display device 4 so as to allow an image to be output onto other media such as paper via the printer.

The portable type recording medium 5 is a portable type recording medium for transferring information from the processor 7 of the extracorporeal receiving apparatus 3 to the display device 4, and is constituted of, for example, a CompactFlash (registered trademark) memory or the like. The portable type recording medium 5 is configured to be attachable/detachable to/from the processor 7 and the display device 4, and has a structure in which information can be output therefrom or recorded thereon when the medium 5 is attached to the display device 4 or the processor 7. More specifically, while the capsule type endoscope 2 moves through the body cavity of the subject 1, the portable type recording medium 5 is attached to the processor 7, and information on an image of the inside of the subject 1 from the capsule type endoscope 2 is recorded on the medium 5. Further, after the capsule type endoscope 2 is excreted from the subject 1, the portable type recording medium 5 is taken out from the processor 7 to be attached to the display device 4, and image display is performed on the basis of the information read out by the display device 4. Data is transferred from the processor 7 to the display device 4 by the portable type recording medium 5, making it possible for the subject 1 to move freely, even when the capsule type endoscope 2 moves through the inside of the subject 1 unlike the case where the processor 7 and the display device 4 are connected to each other by a cable.

Figure 2:
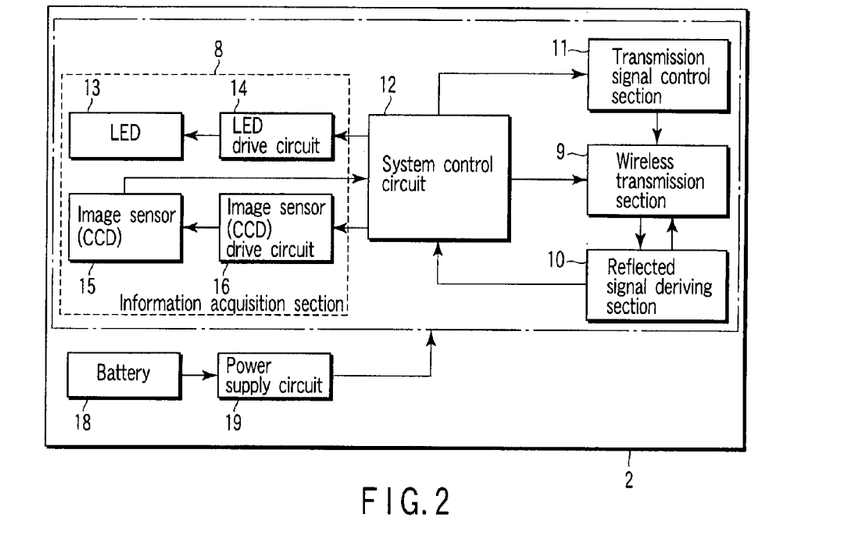
FIG. 2 is a block diagram showing a detailed configuration of a capsule type endoscope.

FIG. 2 is a block diagram showing a detailed configuration of the capsule type endoscope 2. The capsule type endoscope 2 comprises a battery 18, a power supply circuit 19, an information acquisition section 8, a wireless transmission section 9, a reflected signal deriving section 10, a transmission signal control section 11, and a system control circuit 12.

The battery 18 is a power source for supplying power used inside the capsule type endoscope 2. The power supply circuit 19 generates power to be supplied to each constituent element inside the capsule type endoscope 2 from the power supplied from the battery 18 and supplies the generated power to each constituent element in the capsule type endoscope 2. Each constituent element in the capsule type endoscope 2 operates by using power supplied from the power supply circuit 19 as drive energy.

The information acquisition section 8 is provided with an LED 13, an LED drive circuit 14, an image sensor (CCD) 15, and an image sensor (CCD) drive circuit 16. The LED 13 is a light source for illuminating a region to be imaged inside the subject 1 when the inside of the subject 1 is to be imaged. The LED drive circuit 14 is a drive circuit for driving the LED 13. The CCD 15 is an image sensor of the CCD system for imaging a reflected light image from the region to be imaged illuminated by the LED 13 so as to acquire intra-subject information (image signal). The CCD drive circuit 16 is a drive circuit for driving the CCD 15.

It is not essential to use an LED and an image sensor of the CCD system as the light source and the image sensor of the information acquisition section 8. For example, an image sensor of the CMOS system may be used as the image sensor.

The wireless transmission section 9 generates a transmission signal of a predetermined frequency from the intra-subject information obtained by the information acquisition section 8 and input thereto via the system control circuit 12, and transmits the generated transmission signal to the extracorporeal receiving apparatus 3.

The reflected signal deriving section 10 derives a reflected signal of the transmission signal transmitted from the wireless transmission section 9 resulting from an impedance mismatch between the wireless transmission section 9 and the subject 1.

The transmission signal control section 11 controls the transmission signal transmitted from the wireless transmission section 9 on the basis of an intensity of a reflected signal derived by the reflected signal deriving section 10.

The system control circuit 12 collectively controls operations of the information acquisition section 8, wireless transmission section 9, reflected signal deriving section 10, transmission signal control section 11, and power supply circuit 19.

Figure 3:
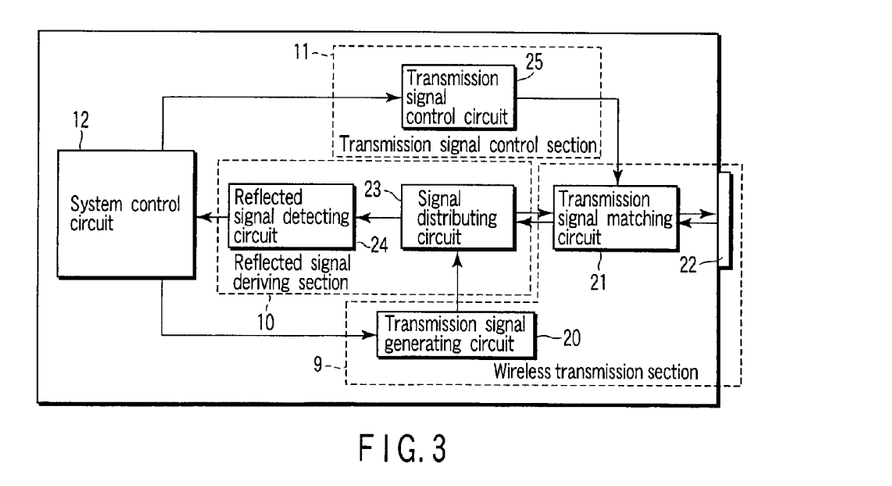
FIG. 3 is a block diagram related to feedback control for stably transmitting a transmission signal in a capsule type endoscope.

FIG. 3 is a block diagram related to feedback control for stably transmitting a transmission signal of the capsule type endoscope 2. Specifically, the feedback control is performed by the system control circuit 12, wireless transmission section 9, reflected signal deriving section 10, and transmission signal control section 11.

The wireless transmission section 9 is provided with a transmission signal generating circuit 20, a transmission signal matching circuit 21, and a transmitting electrode 22. The transmission signal generating circuit 20 subjects image data of the subject 1 input from the system control circuit 12 to processing such as modulation and the like, thereby generating a transmission signal to be transmitted to the extracorporeal receiving apparatus 3. The transmission signal matching circuit 21 changes the characteristic of the transmission signal generated by the transmission signal generating circuit 20 in order to match the output impedance between the transmitting electrode 22 and the subject 1. The transmission signal matching circuit 21 is provided with a function of making the characteristic impedance of the transmission signal variable in the circuit. More specifically, the transmission signal matching circuit 21 is configured to make the impedance constituted of a capacitive component, inductive component, and resistive component variable by receiving a voltage control signal from the transmission signal control section 11. For example, a configuration in which a variable impedance element is connected in series to or in parallel with the transmitting electrode 22 can be employed as the transmission signal matching circuit 21. By means of the transmission signal matching circuit 21 having the configuration described above, it is possible to change the characteristics such as the characteristic impedance of the transmission signal, power of the transmission signal, a phase of the transmission signal, a frequency of the transmission signal, and the like.

Incidentally, when a feedback oscillator circuit is used as the transmission signal generating circuit 20, it is also possible to change the transmission signal frequency in the transmission signal generating circuit 20. In this case too, when the voltage control signal from the system control circuit 12 is received by the transmission signal generating circuit 20, the transmission signal frequency is changed.

The transmitting electrode 22 is an electrode for transmitting the transmission signal to the extracorporeal receiving apparatus 3 via the inside of the subject 1. Here, the transmitting electrode 22 is formed of a member having electrical conductivity, and at least one transmitting electrode is arranged on the outer surface of the capsule type endoscope 2.

The reflected signal deriving section 10 is provided with a signal distributing circuit 23 and a reflected signal detecting circuit 24. The signal distributing circuit 23 distributes the transmission signal input from the transmission signal generating circuit 20 and the reflected signal of the transmission signal resulting from an impedance mismatch between the transmitting electrode 22 and the inside of the subject 1 and input from the transmission signal matching circuit 21, so as to cause the transmission signal to be derived by the transmission signal matching circuit 21, and cause the reflected signal to be derived by the reflected signal detecting circuit 24. Specifically, the signal distributing circuit 23 functions as a directional coupling circuit using a lumped constant element. However, as for the signal distributing circuit 23, a circulator circuit, a 3 dB hybrid distributing circuit, and the like may be used as the constituent elements of the distributing circuit, and the distributing circuit may be constituted of distributed constant elements such as a microstrip line or the like. The reflected signal detecting circuit 24 detects an intensity of a reflected signal derived from the signal distributing circuit 23, and transmits reflected signal intensity data to the system control circuit 12. Specifically, the reflected signal detecting circuit 24 is configured to detect a reflected signal having a frequency similar to that of the transmission signal by using a rectification circuit and a wave detecting circuit, and convert the detected reflected signal into reflected signal intensity data, which is a digital signal, by using an A/D converter circuit.

The transmission signal control section 11 is constituted of a transmission signal control circuit 25. The transmission signal control circuit 25 controls the constituent element of the transmission signal matching circuit 21 when the intensity data of the reflected signal input to the system control circuit 12 does not satisfy the impedance matching condition. Further, the transmission signal control circuit 25 also has a function of setting an initial value of a constituent element of the transmission signal matching circuit 21.

The system control circuit 12 determines whether or not the intensity of the reflected signal from the reflected signal detecting circuit 24 exceeds a predetermined threshold for satisfying the impedance matching condition, and controls the operation of the transmission signal control section 11 on the basis of the determination result.

Figure 4:
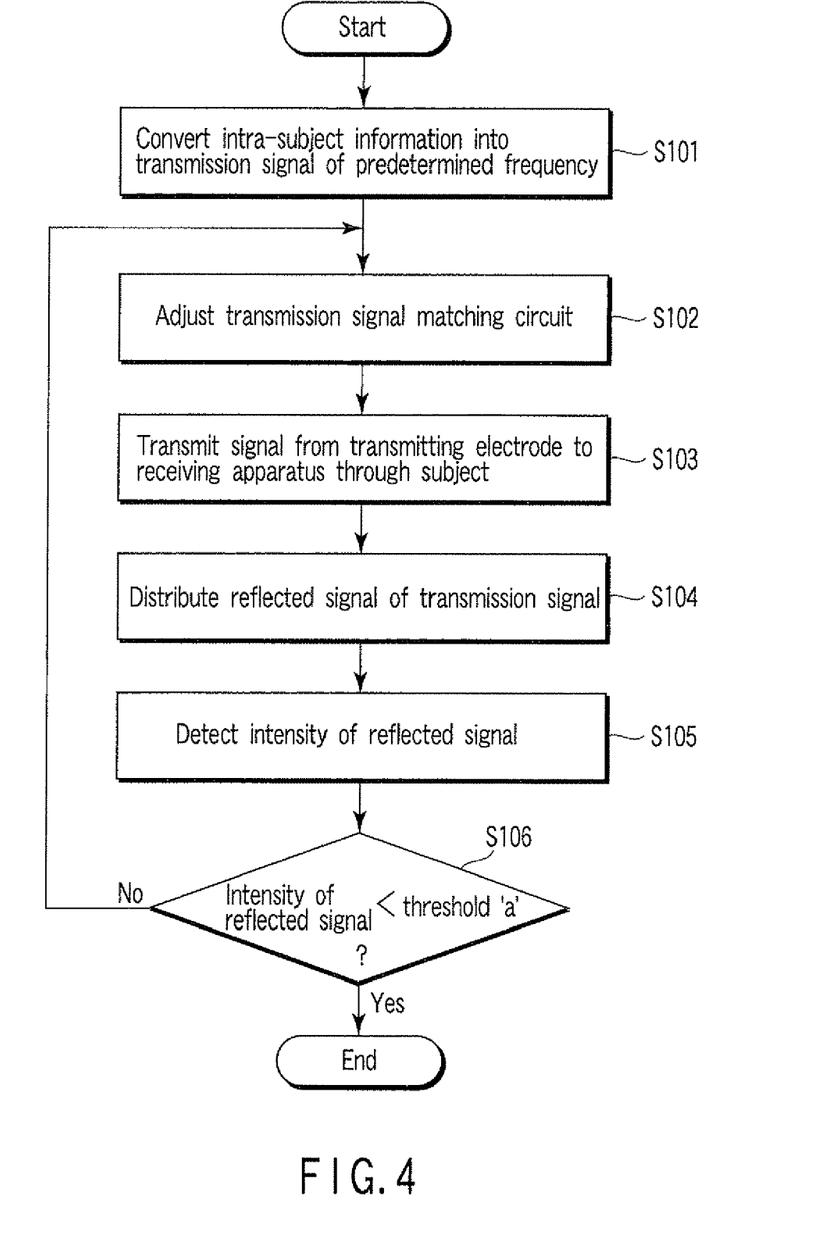
FIG. 4 is a flowchart related to feedback control to be performed in accordance with the configuration shown in FIG. 3.

FIG. 4 is a flowchart related to feedback control to be performed in accordance with the configuration shown in FIG. 3. First, the system control circuit 12 drives the LED 13 through the LED drive circuit 14, and drives the CCD 15 through the CCD drive circuit 16. As a result, the inside of the subject 1 is imaged and an image signal is acquired. The image signal is converted into digital image data by an A/D converter circuit (not shown) constituting the CCD, and is thereafter captured by the system control circuit 12. The system control circuit 12 outputs the captured image data to the transmission signal generating circuit 20 of the wireless transmission section 9. Upon receipt of the image data, the transmission signal generating circuit 20 converts the image data into a transmission signal of a predetermined frequency and outputs the transmission signal to the signal distributing circuit 23 (step S101).

Next, the system control circuit 12 sets the impedance of the constituent element of the transmission signal matching circuit 21 to predetermined impedance through the transmission signal control circuit 25 (step S102).

After the operations described above, the transmission signal generating circuit 20 outputs the generated transmission signal to the signal distributing circuit 23. After the transmission signal is passed through the signal distributing circuit 23 and the transmission signal matching circuit 21, the transmission signal is transmitted from the transmitting electrode 22 to the extracorporeal receiving apparatus 3 through the subject 1 (step S103). In this case, when the transmission signal is transmitted from the transmitting electrode 22 to the extracorporeal receiving apparatus 3 through the subject 1, reflected signal power is caused by the impedance mismatch between the transmitting electrode 22 and the subject 1 resulting from a change in the state of contact between the transmitting electrode 22 and the inside of the subject 1. The reflected signal power $P_R$ caused by the impedance mismatch is obtained on the basis of transmission signal power $P_T$ and a voltage reflection coefficient $\Gamma$. Specifically, it is assumed here that the characteristic impedance of the transmission signal at the output section is $Z_0$, and load impedance of the subject is $Z_L$. Then, the reflection coefficient $\Gamma$ is expressed as $\Gamma=(Z_L-Z_0)/(Z_L+Z_0)$, and reflected signal power $P_R=|\Gamma|^2 \times P_T$ is generated. The signal distributing circuit 23 distributes the reflected signal so as to allow it to be derived at the reflected signal detecting circuit 24 (step S104).

Upon receipt of the reflected signal, the reflected signal detecting circuit 24 detects the intensity of the reflected signal derived from the signal distributing circuit 23 (step S105). The detected intensity data of the reflected signal is utilized by the system control circuit 12 in determination of the impedance matching condition. The system control circuit 12 compares the reflected signal intensity detected by the reflected signal detecting circuit 24 with the threshold 'a' related to the impedance matching condition (step S106). When the intensity of the reflected signal is larger than the threshold 'a' in the determination in step S106, the flow returns to step S102, and the system control circuit 12 sets the impedance of the constituent element of the transmission signal matching circuit 21 again through the transmission signal control circuit 25. On the other hand, when the intensity of the reflected signal is smaller than the threshold 'a', the system control circuit 12 terminates the feedback control.

By performing the feedback control as described above, it is possible to correct the influence of the impedance mismatch resulting from the movement of the capsule type endoscope 2 within the interior of the body of the subject 1 on the capsule type endoscope 2 side and perform stable transmission of intra-subject information.

Figure 5:
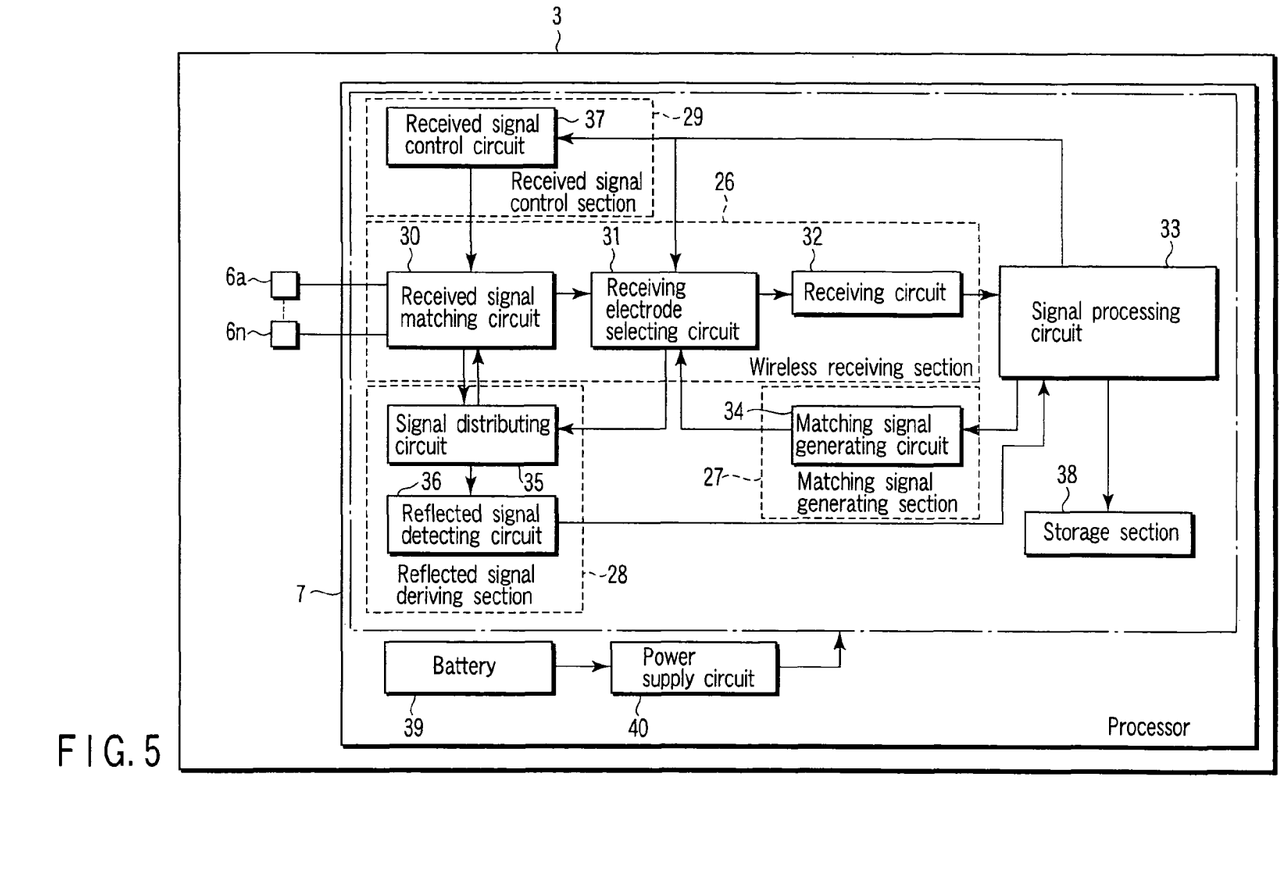
FIG. 5 is a block diagram showing a detailed configuration of an extracorporeal receiving apparatus.

FIG. 5 is a block diagram showing a detailed configuration of the extracorporeal receiving apparatus 3. As described above, the extracorporeal receiving apparatus 3 is provided with the receiving electrodes 6a to 6n and the processor 7. In this embodiment, the above-mentioned feedback control can also be performed in the extracorporeal receiving apparatus 3.

The receiving electrodes 6a to 6n are electrodes formed of a material having electrical conductivity, and used to receive the transmission signal transmitted from the capsule type endoscope 2 through the inside of the subject 1. Incidentally, 'n' is an arbitrary natural number and corresponds to the number of electrodes.

The processor 7 is provided with a battery 39, a power supply circuit 40, a wireless receiving section 26, a matching signal generating section 27, a reflected signal deriving section 28, a received signal control section 29, a signal processing circuit 33, and a storage section 38.

The battery 39 is a power source for supplying power used inside the processor 7. The power supply circuit 40 generates power to be supplied to each constituent element inside the processor 7 from the power supplied from the battery 39 and supplies the generated power to each constituent element in the processor 7. Each constituent element in the processor 7 operates by using power supplied from the power supply circuit 40 as drive energy.

The wireless receiving section 26 is provided with a received signal matching circuit 30, a receiving electrode selecting circuit 31, and a receiving circuit 32. The received signal matching circuit 30 performs impedance matching between the receiving electrodes 6a to 6n and the subject 1. The receiving electrode selecting circuit 31 detects intensities of signals received by the received signal matching circuit 30 through the receiving electrodes 6a to 6n, selects the optimum received signal, i.e., the received signal having the highest intensity on the basis of the detected intensities, and outputs the selected received signal to the receiving circuit 32. The receiving circuit 32 subjects the received signal to predetermined processing such as demodulation, and derives the intra-subject information (image data) acquired by the capsule type endoscope 2 from the received signal.

The matching signal generating section 27 generates a matching signal for stably receiving a transmission signal from the capsule type endoscope 2. The matching signal generating section 27 is provided with a matching signal generating circuit 34 for generating a matching signal.

The reflected signal deriving section 28 is provided with a signal distributing circuit 35 and a reflected signal detecting circuit 36. The signal distributing circuit 35 distributes a matching signal generated by the matching signal generating section 27 and a reflected signal of the matching signal from each of the receiving electrodes 6a to 6n so as to cause the matching signal to be derived by the received signal matching circuit 30 and cause the reflected signal to be derived by the reflected signal detecting circuit 36. The reflected signal detecting circuit 36 detects the intensity of the reflected signal of the matching signal distributed by the signal distributing circuit 35, and outputs the intensity data to the signal processing circuit 33. Incidentally, as the configuration of the reflected signal detecting circuit 36, the same configuration as that of the reflected signal detecting circuit 24 may be used.

The received signal control section 29 controls the constituent element of the received signal matching circuit 30 when the intensity of the reflected signal input to the signal processing circuit 33 does not satisfy the impedance matching condition. Further, the received signal control section 29 also has a function of setting an initial value of a constituent element of the received signal matching circuit 30.

The signal processing circuit 33 collectively controls the respective sections of the processor 7, and performs image processing necessary for recording image data received through the receiving circuit 32. Further, the signal processing circuit 33 determines whether or not the intensity of the reflected signal detected by the reflected signal detecting circuit 24 exceeds the predetermined threshold satisfying the impedance matching condition, and controls the operation of the received signal control section 29 on the basis of the determination result. The storage section 38 stores image data which has been subjected to image processing. Incidentally, image data which has been subjected to image processing by the signal processing circuit 33 can also be recorded on the portable type recording medium 5 as described above.

Figure 6:
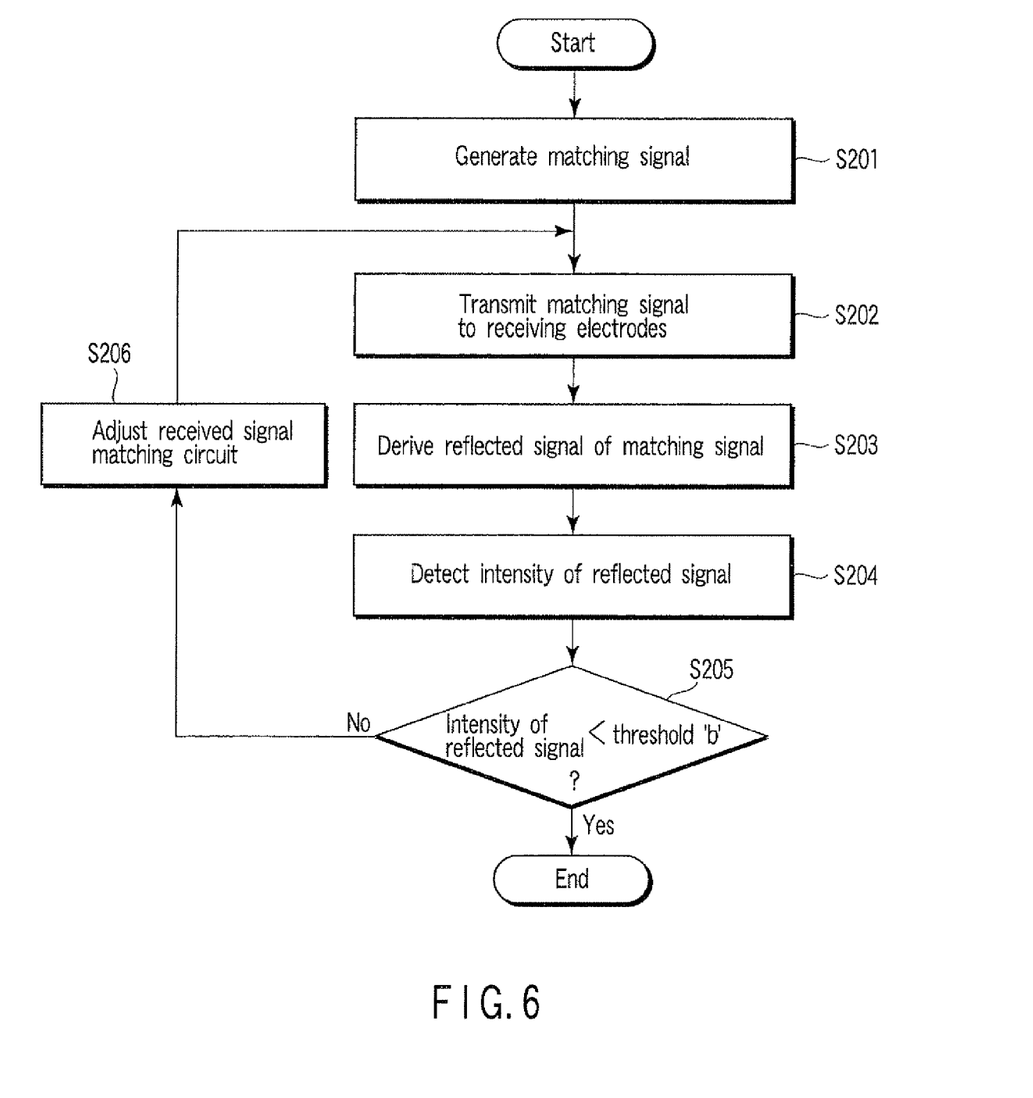
FIG. 6 is a flowchart related to feedback control to be performed in accordance with the configuration shown in FIG. 5.

FIG. 6 is a flowchart related to feedback control to be performed in accordance with the configuration shown in FIG. 5. First, the signal processing circuit 33 controls the matching signal generating circuit 34 of the matching signal generating section 27 to generate a matching signal (step S201). Here, it is desirable that a period other than a period in which a transmission signal from the capsule type endoscope 2 is received be set as an operation period of the matching signal generating circuit. Further, it is effective to use a signal having frequency components equal to those of the transmission signal of the capsule type endoscope 2 as the matching signal. However, the present invention is not limited to this, and a continuous wave signal of a single frequency including a frequency component of the transmission signal may be used as the matching signal.

Next, the matching signal generating circuit 34 outputs the generated matching signal to the receiving electrodes 6a to 6n (step S202). When the matching signal is transmitted to the receiving electrodes 6a to 6n, a reflected signal having a magnitude corresponding to the impedance mismatch between the receiving electrodes 6a to 6n and the subject 1 is generated. The signal distributing circuit 35 distributes a reflected signal starting from the receiving electrodes 6a to 6n and directed to the receiving circuit 32 such that the reflected signal is derived by the reflected signal detecting circuit 36 (step S203).

Upon receipt of the reflected signal, the reflected signal detecting circuit 36 detects the intensity of the reflected signal (step S204). The detected intensity data of the reflected signal is utilized by the signal processing circuit 33 for determining the impedance matching condition. The signal processing circuit 33 compares the intensity of the reflected signal detected by the reflected signal detecting circuit 36 with the threshold 'b' related to the impedance mismatch (step S205). In the determination in step S205, when the intensity of the reflected signal is larger than the threshold 'b', the signal processing circuit 33 sets the impedance of the constituent element of the received signal matching circuit 30 through the received signal control circuit 37 (step S206). On the other hand, when the intensity of the reflected signal is smaller than the threshold 'b', the signal processing circuit 33 terminates the feedback control.

By performing the feedback control as described above, it is possible to correct the influence of the impedance mismatch between the subject 1 and the receiving electrodes 6a to 6n on the extracorporeal receiving apparatus 3 side and perform stable reception of intra-subject information.

As has been described above, according to this embodiment, with respect to the output impedance changing between the capsule type endoscope 2 which is introduced into the inside of the subject 1 and moves therethrough and the subject 1, feedback control is performed by utilizing the intensity of the reflected signal having a relationship with an amount of a change in the output impedance, whereby it becomes possible to supply stable transmission signal power to the subject 1. The transmission signal of the predetermined frequency including the image data acquired by the capsule type endoscope 2 is transmitted to the subject 1 through the transmitting electrode 22. At this time, with respect to the impedance mismatch generated when the state of contact between the transmitting electrode 22 and the subject 1 is changed and the output impedance is changed, feedback control is performed in such a manner that the intensity of the reflected signal is reduced, by using the signal distributing circuit 23, reflected signal detecting circuit 24, system control circuit 12, transmission signal control circuit 25, and transmission signal matching circuit 21, whereby it is possible to maintain the state where the transmission power loss is small. Accordingly, it becomes possible for the capsule type endoscope 2 to continuously supply stable transmission power to the subject 1.

Furthermore, likewise, in the extracorporeal receiving apparatus 3, with respect to the impedance mismatch generated between the subject 1 and the receiving electrodes 6a to 6n, feedback control using the intensity of the reflected signal of the matching signal generated by the matching signal generating circuit 34 in the processor 7 is performed, whereby it is possible to stably receive the transmission signal of the capsule type endoscope 2.

In this embodiment, although feedback control is performed both the capsule type endoscope 2 and the extracorporeal receiving apparatus 3 which constitute the intra-subject information system, the feedback control may be performed either only in the capsule type endoscope 2 or the extracorporeal receiving apparatus 3.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An intro-subject introduction apparatus which is introduced into the inside of a subject and is movable inside the subject, comprising:
    an information acquisition section which acquires intra-subject information;
    a wireless transmission section which transmits a transmission signal including the acquired intra-subject information to an extracorporeal receiving apparatus provided outside the subject;
    a reflected signal deriving section which derives a reflected signal generated between the wireless transmission section and the inside of the subject; and
    a transmission signal control section which controls the wireless transmission section on the basis of the derived reflected signal.

2. The intro-subject introduction apparatus according to claim 1, wherein
    the wireless transmission section includes:
    a signal generating section which generates the transmission signal of a predetermined frequency from the intra-subject information;
    at least one transmitting electrode which is arranged on an outer surface of the intro-subject introduction apparatus, and transmits the transmission signal to the extracorporeal receiving apparatus through the subject; and
    a transmission signal matching section which changes a characteristic of a transmission signal generated by the signal generating section.

3. The intro-subject introduction apparatus according to claim 1, wherein
    the reflected signal deriving section includes:
    a signal distributing section which distributes the transmission signal and the reflected signal; and a reflected signal detecting section which detects the distributed reflected signal.

4. The intro-subject introduction apparatus according to claim 2, wherein the transmission signal control section changes one of circuit impedance of the wireless transmission section, a frequency of the transmission signal, power of the transmission signal, and a phase of the transmission signal by the transmission signal matching section on the basis of a reflected signal derived by the reflected signal deriving section.

5. An extracorporeal receiving apparatus arranged outside a subject, comprising:
- a wireless receiving section which receives a transmission signal including intra-subject information from an intro-subject introduction apparatus which is introduced into the inside of a subject and is movable inside the subject;
- a matching signal generating section which generates a matching signal for a match between the wireless receiving section and the subject;
- a reflected signal deriving section which derives a reflected signal of a matching signal generated between the wireless receiving section and the subject; and
- a received signal control section which controls the wireless receiving section on the basis of the derived reflected signal.

6. The extracorporeal receiving apparatus according to claim 5, wherein
the wireless receiving section includes:
- at least one receiving electrode which is arranged on an outer surface of the subject, and receives the transmission signal from the intro-subject introduction apparatus through the subject; and
- a received signal matching section which changes a characteristic of the received transmission signal.

7. The extracorporeal receiving apparatus according to claim 5, wherein
the reflected signal deriving section includes:
- a signal distributing section which distributes the matching signal and the reflected signal; and
- a reflected signal detecting section which detects the distributed reflected signal.

8. The extracorporeal receiving apparatus according to claim 6, wherein the received signal control section changes one of circuit impedance of the wireless receiving section, a frequency of the transmission signal received from the receiving electrode, power of the transmission signal, and a phase of the transmission signal by the received signal matching section on the basis of a reflected signal derived by the reflected signal deriving section.

9. An intra-subject information gathering system comprising:
an intro-subject introduction apparatus which is introduced into the inside of a subject and is movable inside the subject, including:
(a) an information acquisition section which acquires intra-subject information;
(b) a wireless transmission section which transmits a transmission signal including the intra-subject information acquired by the information acquisition section;
(c) a transmitting side reflected signal deriving section which derives a reflected signal generated between the wireless transmission section and the inside of the subject; and
(d) a transmission signal control section which controls the wireless transmission section on the basis of the reflected signal derived by the transmitting side reflected signal deriving section; and
an extracorporeal receiving apparatus arranged outside the subject, including:
(a) a wireless receiving section which receives the transmission signal from the intro-subject introduction apparatus;
(b) a matching signal generating section which generates a matching signal for a match between the wireless receiving section and the subject;
(c) a receiving side reflected signal deriving section which derives a reflected signal of a matching signal generated between the wireless receiving section and the subject; and
(d) a received signal control section which controls the wireless receiving section on the basis of the reflected signal derived by the receiving side reflected signal deriving section.

* * * * *